United States Patent [19]

Takayama et al.

[11] 4,110,462
[45] Aug. 29, 1978

[54] N'-SULFENYL-N"-DIHALO-PHENYLIMIDAZOLIDINEDIONES

[75] Inventors: Chiyozo Takayama, Toyonaka; Shigeo Yamamoto, Sanda; Toshiro Kato, Ibaraki; Yoshio Hisada, Kawanishi; Akira Fujinami, Takarazuka, all of Japan

[73] Assignee: Sumitomo Chemical Company, Limited, Japan

[21] Appl. No.: 747,109

[22] Filed: Dec. 3, 1976

[30] Foreign Application Priority Data

Dec. 22, 1975 [JP] Japan .................. 50-154513

[51] Int. Cl.² ...................... C07D 233/80; A01N 9/12
[52] U.S. Cl. .................. 424/273 R; 548/311
[58] Field of Search .............. 260/309.5; 424/273; 548/311

[56] References Cited

U.S. PATENT DOCUMENTS

| | | | |
|---|---|---|---|
| 3,177,224 | 4/1965 | Cremlyn et al. | 260/309.5 |
| 3,499,030 | 3/1970 | Kuhle et al. | 260/309.5 |
| 3,668,217 | 6/1972 | Fujinami et al. | 260/309.5 |
| 3,960,883 | 6/1976 | Hubele | 260/309.5 |

OTHER PUBLICATIONS

Hubele II, Chem. Abst. 1975, vol. 82, No. 170955a.
Clapot et al., Chem. Abst. 1976, vol. 84, No. 44048k.

Primary Examiner—Natalie Trousof
Attorney, Agent, or Firm—Birch, Stewart, Kolasch and Birch

[57] ABSTRACT 3-(3',5'-Dihalophenyl)-1-sulfenylimidazolidine-2,4-diones of the formula:

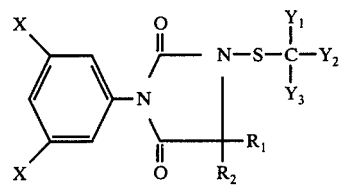

wherein X is a chlorine atom or a bromine atom, $Y_1$, $Y_2$ and $Y_3$ are each a chlorine atom or a fluorine atom and $R_1$ and $R_2$ are individually a hydrogen atom or a methyl group, which show high microbicidal activities against various fungi without any material toxicity to mammals and plants and can be produced by reacting the corresponding 1-unsubstituted compound with a sulfenyl halide.

5 Claims, No Drawings

N'-SULFENYL-N''-DIHALOPHENYLIMIDAZOLI-DINEDIONES

The present invention relates to 3-(3',5'-dihalophenyl)-1-sulfenylimidazolidine-2,4-diones (hereinafter referred to as "1-sulfenylimidazolidinedione(s)") of the formula:

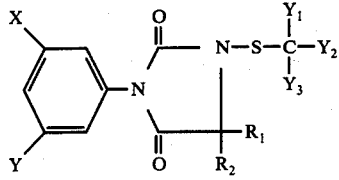
(I)

wherein X is a chlorine atom or a bromine atom, $Y_1$, $Y_2$ and $Y_3$ are each a chlorine atom or a fluorine atom and $R_1$ and $R_2$ are individually a hydrogen atom or a methyl group, and their preparation and use.

Specific compounds include those wherein X is a chlorine atom, $Y_1$, $Y_2$ and $Y_3$ are each a chlorine atom or a fluorine atom and each of $R_1$ and $R_2$ is a hydrogen atom, or wherein each of X, $Y_1$, $Y_2$ and $Y_3$ is a chlorine atom and each of $R_1$ and $R_3$ is a hydrogen atom.

It is already well known that some of the 3-(3',5'-dihalophenyl)imidazolidine-2,4-dione derivatives, of which the 1- and 5-positions may be optionally substituted with various substituents, have an antimicrobial activity on certain microorganisms (U.S. Pat. Nos. 3,668,217 and 3,716,552). As the results of an extensive study, it has now been found that the said compounds (I) having a trihalogenomethanesulfenyl group at the 1-position exhibit an antimicrobial activity which is widely applicable and markedly superior as compared with their homologues, and in addition show no material phytotoxicity to plants.

The 1-sulfenylimidazolidinediones (I) have prominent effects on such a wide scope of fungi as *Pyricularia oryzae, Cochliobolus miyabeanus, Pellicularia sasakii, Glomerella cingulata, Sclerotinia sclerotiorum, Sclerotinia cinerea, Botrytis cinerea, Alternaria mali, Sclerotinia mali, Mycosphaerella melonis, Alternaria kikuchiana, Alternaria brassicicola, Penicillium italicum* and *Pythium* spp. They can control simultaneously two or more of said fungi and are quite excellent as phytopathogenic microbecontrolling agents. Also, they can effectively control *Aspergillus niger* which propagates in industrial products and hence are excellent as industrial microbicides. Advantageously, they are extremely low toxicity and have little detrimental actions on mammals and fishes.

A main object of the present invention is to provide novel 1-sulfenylimidazolidinediones (I), which are useful as microbicides. Another object of this invention is to provide a process for producing such 1-sulfenylimidazolidinediones (I). A further object of the invention is to provide microbicidal compositions containing such 1-sulfenylimidazolidinediones (I). These and other objects and advantages of the invention will become apparent from the foregoing and subsequent descriptions.

The 1-sulfenylimidazolidinediones (I) can be prepared by reacting the corresponding 1-unsubstituted compound of the formula:

(II)

wherein X, $R_1$ and $R_2$ are each as defined above, with a sulfenyl halide of the formula:

$$Z-S-\underset{\underset{Y_3}{|}}{\overset{\overset{Y_1}{|}}{C}}-Y_2 \qquad (III)$$

wherein $Y_1$, $Y_2$ and $Y_3$ are each as defined above and Z is a halogen atom.

The reaction is usually carried out by stirring a mixture of the starting 1unsubstituted compound (II) with an equivalent or excessive molar amount of the sulfenyl halide (III) at room temperature (0°– 35° C) in the presence or absence of an inert solvent (e.g., benzene, toluene, xylene, tetrahydrofuran, dioxane, chlorobenzene, chloroform, carbon tetrachloride, nitrobenzene). When desired, the reaction may be performed while heating (up to reflux) and/or in the presence of a dehydrohalogenating agent (e.g., pyridine, triethylamine, N-methylmorpholine, dimethylaniline, diethylaniline, sodium hydride, sodium amide, sodium methoxide, sodium ethoxide) so as to accomplish the production of the objective compound smoothly.

The starting 1-unsubstituted compound (II) is obtainable, for instance, by the process as described in U.S. Pat. No. 3,668,217. Examples of such 1-unsubstituted compound (II) include:

1. 3-(3',5'-Dichlorophenyl)imidazolidine-2,4-dione;
2. 3-(3',5'-Dibromophenyl)imidazolidine-2,4-dione;
3. 3-(3',5'-Dichlorophenyl)-5-methylimidazolidine-2,4-dione;
4. 3-(3',5'-Dichlorophenyl)-5,5-dimethylimidazolidine-2,4-dione;
5. 3-(3',5'-Dibromophenyl)-5-methylimidazoline-2,4-dione; and
6. 3-(3',5'-Dibromophenyl)-5,5-dimethylimidazolidine-2,4-dione. Examples of the sulfenyl halide (III) are as follows:

7. Trichloromethanesulfenyl chloride;
8. Dichlorofluoromethanesulfenyl chloride;
9. Chlorodifluoromethanesulfenyl chloride;
10. Trifluoromethanesulfenyl chloride;
11. Trichloromethanesulfenyl bromide;
12. Dichlorofluoromethanesulfenyl bromide;
13. Chlorodifluoromethanesulfenyl bromide; and
14. Trifluoromethanesulfenyl bromide, etc.

In actual application as microbicides, the 1-sulfenylimidazolidinediones (I) may be used alone without incorporation of any other ingredients such as carriers and diluents or, for easier application, in admixture with such solid carriers or diluents as talc, clay and the like or with such liquid carriers or diluents as organic solvents and the like. The microbicidal compositions can be formulated into any of the ordinarily adopted forms such as, for example, dusts, wettable powders, oil sprays, aerosols, tablets, emulsifiable concentrates and granules.

Further, the 1-sulfenylimidazolidinediones (I) may be used in admixture with other chemicals such as, for example, Blasticidin-S, Kasugamycin, Polyoxin, acetylene dicarboximide, 3-[2-(3,5-dimethyl-2-oxocyclohexyl)-2-hydroxyethyl]glutarimide, streptomycin, griseofluvin, pentachloronitrobenzene, pentachlorophenol, hexachlorobenzene, pentachlorobenzyl alcohol, pentachlorobenzaldoxime, 2,6-dichloro-4-nitroaniline, zinc ethylene bisdithiocarbamate, zinc dimethyl thiocarbamate, manganese ethylene bisdithiocarbamate, bis(-dimethylthiocarbamoyl) disulfide, 2,4,5,6-tetrachloroisophthalonitrile, 2,3-dichloro-1,4-naphthoquinone, tetrachloro-p-benzoquinone, p-dimethylaminobenzenediazo sodium sulfonate, 2-(1-methylheptyl)-4,6-dinitrophenyl crotonate, 2-heptadecylimidazoline acetate, 2,4-dichloro-6-(o-chloroanilino)-s-triazine, dodecylguanidine acetate, 6-methyl-2,3-quinoxalinedithiol cyclic-S,S-dithiocarbonate, 2,3-quinoxalinedithiol cyclic trithiocarbonate, N-trichloromethylthio-4-cyclohexene-1,2-dicarboximide, N-(1,1,2,2-tetrachlorethylthio)-4-cyclohexene-1,2-dicarboximide, N-(3,',5'-dichlorophenyl) maleinimide, N-(3',5'-dichlorophenyl) succinimide, N-(3',5'-dichlorophenyl) itaconimide, 3-(3',5'-dichlorophenyl)-5,5-dimethyloxazolidine-2,4-dione, 2,3-dihydro-5-carboxanilide-6-methyl-1,4-oxazine-4,4-dioxide, 2,3-dihydro-5-carboxanilide-6-methyl-1,4-oxazine, 1-(N-n-butylcarbamoyl)-2-methoxycarbonylaminobenzimidazole, O,O-diethyl-S-benzyl phosphorothioate, O-ethyl-S,S-diphenyl phosphorodithioate, O-ethyl-O-phenyl-O-(2,4,5-trichlorophenyl) phosphate, O,O-dimethyl-O-(3-methyl-4-nitrophenyl) phosphorothioate, S-[1,2-bis(ethoxycarbonyl)ethyl]-O,O-dimethyl phosphorodithioate, O,O-dimethyl-S-(N-methylcarbamoylmethyl) phosphorodithioate, O,O-diethyl-O-(2-isopropyl-6-methyl-4-pyrimidyl) thiophosphate, 3,4-dimethylphenyl-N-methylcarbamate, iron methylarsonate, 2-chloro-4,6-bis-(ethylamino)-s-triazine, 2,4-dichlorophenoxyacetic acid (including its salts and esters), 2-methyl-4-chlorophenoxyacetic acid (including its salts and esters), 2,4-dichloro-phenyl-4'-nitrophenyl ether, sodium pentachlorophenolate, N-(3,4-dichlorophenyl) propionamide, 3-(3',4'-dichlorophenyl)-1,1-dimethylurea, α,α,α-trifluoro-2,6-dinitro-N,N-di-n-propyl-p-toluidine, 2-chloro-2',6'-diethyl-N-(methoxymethyl) acetamide, 1-naphthyl-N-methylcarbamate, methyl-N-(3,4-dichlorophenyl) carbamate, 4-chlorobenzyl-N,N-dimethylthiol carbamate, N,N-diallyl-2-chloroacetamide, ethyl-β-(2,4-dichlorophenoxy) acrylate and cyclohexyl-β-(2,4-dichlorophenoxy) acrylate; and, in every case, the controlling effects of the individual chemicals are not decreased. Accordingly, simultaneous control of two or more pests and injurious insects is possible. In addition thereto, they may be used in admixture with such agricultural chemicals as insecticides and miticides and with fertilizers.

Practical and presently preferred embodiments of the present invention are illustratively shown in the following examples, wherein parts and % are by weight.

EXAMPLE 1

Preparation of the 1-sulfenylimidazolidinediones (I):

A mixture of 0.05 mole of the 1-unsubstituted compound (II) and 0.06 mole of triethylamine is dissolved in 100 ml of tetrahydrofuran, and 0.07 mole of the sulfenyl halide (III) is dropwise added thereto with stirring at room temperature. The resulting mixture is heated under reflux for 2 hours. After completion of the reaction, excess of the sulfenyl halide (III), triethylamine and tetrahydrofuran are removed by evaporation, and the residue is washed several times with water and dried to give the 1-sulfenylimidazolidinedione (I). If necessary, the product may be recrystallized from ethanol or benzene/hexane for purification.

Examples of the 1-sulfenylimidazolidinedione (I) are shown in Table 1.

Table 1

| Starting materials | | | | Produced 1-sulfenylimidazolidinedione (I) | | | | | | |
|---|---|---|---|---|---|---|---|---|---|---|
| 1-Unsubstituted compound (II) | Sulfenyl-halide (III) | No. | Chemical structure | Physical constant | Yield (%) | Elementary analysis (%) | | | | |
| | | | | | | C | H | N | S | Cl |
| 1 | 7 | 15 | Cl-C6H3(Cl)-N(C(=O)-N-SCCl3)(C(=O)-CH-H) | M.P. 169.5–171.5° C | 92 | 30.45 (30.49) | 1.28 (1.41) | 7.10 (7.02) | 8.13 (7.90) | 44.94 (44.79) |
| 4 | 7 | 16 | Cl-C6H3(Cl)-N(C(=O)-N-SCCl3)(C(=O)-C(CH3)2) | M.P. 126.0–128.0° C | 79 | 34.11 (34.00) | 2.15 (2.03) | 6.63 (6.82) | 7.59 (7.37) | 41.95 (42.13) |
| 2 | 7 | 17 | Br-C6H3(Br)-N(C(=O)-N-SCCl3)(C(=O)-CH-H) | M.P. 165.5–168.5° C | 85 | 24.85 (24.70) | 1.04 (1.28) | 5.80 (5.59) | 6.63 (6.88) | — |

Table 1-continued

| Starting materials | | Produced 1-sulfenylimidazolidinedione (I) | | | | | | | |
| 1-Unsubstituted compound (II) | Sulfenyl-halide (III) | No. | Chemical structure | Physical constant | Yield (%) | Elementary analysis (%) | | | | |
| | | | | | | C | H | N | S | Cl |
| 1 | 8 | 18 | (structure: 2,4-dichlorophenyl imidazolidinedione N—SCCl$_2$F) | M.P. 134.0 –137.0° C | 83 | 31.77 (31.61) | 1.33 (1.53) | 7.41 (7.18) | 8.48 (8.79) | — |

EXAMPLE 2

Formulation of compositions:

a. Dust

3 Parts of the compound (15) and 97 parts of clay were thoroughly pulverized and mixed together to obtain a dust containing 3% of the active ingredient. In application, the dust was dusted as such.

b. Dust

2 Parts of the compound (16) and 98 parts of talc were thoroughly pulverized and mixed together to obtain a dust containing 2% of the active ingredient. In application, the dust was dusted as such.

c. Wettable powder

50 Parts of the compound (17), 5 parts of a wetting agent of the alkylbenzenesulfonate type and 45 parts of diatomaceous earth were thoroughly pulverized and mixed together to obtain a wettable powder containing 50% of the active ingredient. In application, the wettable powder was diluted with water, and the resulting solution was sprayed.

d. Emulsifiable concentrate

10 Parts of the compound (18), 70 parts of dimethyl sulfoxide, 10 parts of toluene and 10 parts of an emulsifier of the polyoxyethylene dodecylphenol ether type were mixed together to obtain an emulsifiable concentrate containing 10% of the active ingredient. In application, the emulsifiable concentrate was diluted with water, and the resulting emulsion was sprayed.

e. Granule

5 Parts of the compound (15), 93.5 parts of clay and 1.5 parts of a binder of the polyvinyl alcohol type were thoroughly pulverized and mixed together, kneaded with water and then granulated and dried to obtain a granule containing 5% of the active ingredient.

The following examples show some typical test data supporting the excellent activity of the 1-sulfenylimidazolidinediones (I). In these examples, the compound numbers correspond to those in Table 1.

Example 3

Protective activity on stem rot of beans (*Sclerotinia sclerotiorum*):

Beans (var.: Nagauzura) were grown up to the primary leaf stage in flower pots of 9 cm in diameter. Each test compound in the form of an emulsifiable concentrate was diluted with water to a required concentration and foliar-sprayed in a proportion of 10 ml/pot. After air-drying for 4 hours, a disc-inoculum (5 mm in diameter) containing *Sclerotinia sclerotiorum* cultured on a potato sucrose agar medium was inoculated on the primary leaves and kept at 20° C for 3 days under a humid condition. Thereafter, the disease severity was checked. As the result, the compounds of the invention showed markedly excellent effects as compared with the control compounds as shown in Table 2. The disease severity was determined as follows:

The rate of disease severity on the primary leaves was classified into six disease indices, 0 to 5, and the number of the leaves, $n_0, n_1, n_2, \ldots n_5$, corresponding to each disease index was checked. Next, the disease severity was calculated according to the following equation:

$$\text{Disease severity} = \frac{0 \times n_0 + 1 \times n_1 + 2 \times n_2 + \ldots + 5 \times n_5}{5 \times (\text{the number of the total leaves checked})} \times 100$$

| Disease appearance | Disease index |
|---|---|
| No infection | 0 |
| Slight infection around the inoculum | 1 |
| Infected area of about one-fifth | 2 |
| Infected area of about two-fifths | 3 |
| Infected area of about three-fifths | 4 |
| Infected area of more than three-fifths | 5 |

The control of disease was calculated according to the following equation:

$$\text{Control of disease} = \frac{\text{Disease severity in the untreated plot} - \text{Disease severity in the treated plot}}{\text{Disease severity in the untreated plot}} \times 100$$

Table 2

| Test compound No. | Concentration (ppm) | Disease severity (%) | Control of disease (%) |
|---|---|---|---|
| 15 | 50 | 0 | 100 |
| | 25 | 0 | 100 |
| 16 | 50 | 0 | 100 |
| | 25 | 0 | 100 |
| 17 | 50 | 0 | 100 |
| | 25 | 0 | 100 |
| 18 | 50 | 0 | 100 |
| | 25 | 0 | 100 |
| (2,4-dichlorophenyl hydantoin structure) *1) | 50 | 76 | 90 |
| | 25 | 100 | 0 |
| 2,6-Dichloro-4-nitro-aniline *2) | 500 | 40 | 60 |
| | 200 | 70 | 30 |
| | 100 | 90 | 10 |
| | 50 | 100 | 0 |

Table 2-continued

| Test compound No. | Concentration (ppm) | Disease severity (%) | Control of disease (%) |
| --- | --- | --- | --- |
| No treatment | — | 100 | — |

Note:
*[1] Disclosed in U.S. Pat. No. 3,668,217.
*[2] Commercially available fungicide known as "Dicloran".

EXAMPLE 4

Protective activity on gray mould of cucumber (*Botrytis cinerea*):

Cucumbers (var.: Kaga Aonaga-fushinari) were grown up to the second true leaf stage in flower pots of 9 cm in diameter. Each test compound in the form of an emulsifiable concentrate was diluted with water to the required concentration and sprayed in a proportion of 10 ml/pot. After air-drying for 4 hours, a disc-inoculum (5 mm in diameter) containing *Botrytis cinerea* cultured on a potato sucrose agar medium was inoculated on the leaves and kept at 20° C for 4 days under a humid condition. Thereafter, the disease severity was checked. As the result, the compounds of the invention showed an excellent protective activity as compared with the control compounds as shown in Table 3. The disease severity and the control of disease were determined in the same manner as in Example 3.

Table 3

| Test compound No. | Concentration (ppm) | Disease severity (%) | Control of disease (%) |
| --- | --- | --- | --- |
| 15 | 50 | 0 | 100 |
|  | 25 | 0 | 100 |
| 16 | 50 | 0 | 100 |
|  | 25 | 0 | 100 |
| 17 | 50 | 0 | 100 |
|  | 25 | 0 | 100 |
| 18 | 50 | 0 | 100 |
|  | 25 | 0 | 100 |
| (Cl-substituted phenyl N,N-cyclic dicarboximide) *[1] | 100 | 14 | 86 |
|  | 50 | 80 | 20 |
|  | 25 | 100 | 0 |
| Trichloromethylthio-tetrahydrophthalimide *[2] | 200 | 10 | 90 |
|  | 100 | 32 | 68 |
|  | 50 | 80 | 20 |
|  | 25 | 100 | 0 |
| No treatment | — | 100 | — |

Note:
*[1] Disclosed in U.S. Pat. No. 3,668,217.
*[2] Commercially available fungicide known as "Captan".

EXAMPLE 5

Protective activity on black spot of chinese cabbage (*Alternaria brassicicola*):

Chinese cabbages (var.: Nagaoka-kohai No. 2) were grown up to the third true leaf stage in flow pots of 9 cm in diameter. Each test compound in the form of an emulsifiable concentrate was diluted with water to the required concentration and foliar-sprayed in a proportion of 10ml/pot. After 4 hours, the spore suspension (200 spores under 150 magnifications) of *Alternaria brassicicola* cultured on a V8 agar medium was inoculated by spraying and kept at 27 to 28° C for 3 days while being maintained at a constant temperature and humidity in the dark. Thereafter, the disease severity was checked. As the result, the compounds of the invention showed markedly excellent effects as compared with the control compounds as shown in Table 4. The disease severity was calculated as follows.

The rate of disease severity of the leaves was classified into five disease indices, 0, 1, 2, 4, 8, and the number of the leaves, $n_0, n_1, n_2, ---n_8$, corresponding to each disease index was checked. Next, the disease severity was calculated according to the following equation:

$$\text{Disease severity} = \frac{0 \times n_0 + 1 \times n_1 + 2 \times n_2 + \ldots + 8 \times n_8}{8 \times (\text{the number of the total leaves checked})} \times 100$$

| Disease appearance | Disease index |
| --- | --- |
| No infectious spot | 0 |
| Infected area of less than 10 % | 1 |
| Infected area of 10 to 25 % | 2 |
| Infected area of 25 to 60 % | 4 |
| Infected area of 50 to 100 % | 8 |

The control of disease was calculated as in Example 3.

Table 4

| Test compound No. | Concentration (ppm) | Disease severity (%) | Control of disease (%) |
| --- | --- | --- | --- |
| 15 | 100 | 0 | 100 |
|  | 50 | 3 | 97 |
|  | 25 | 10 | 90 |
| 16 | 100 | 0 | 100 |
|  | 50 | 0 | 100 |
|  | 25 | 7 | 93 |
| 17 | 100 | 0 | 100 |
|  | 50 | 5 | 95 |
|  | 25 | 20 | 80 |
| 18 | 100 | 0 | 100 |
|  | 50 | 0 | 100 |
|  | 25 | 10 | 90 |
| (Cl-substituted phenyl N,N-cyclic dicarboximide) *[1] | 100 | 40 | 60 |
|  | 50 | 80 | 20 |
|  | 25 | 100 | 0 |
| Trichloromethylthio-tetrahydrophthalimide *[2] | 500 | 7 | 93 |
|  | 200 | 32 | 68 |
|  | 100 | 70 | 30 |
|  | 50 | 100 | 0 |
|  | 25 | 100 | 0 |
| No treatment | — | 100 | — |

Note:
*[1] Disclosed in U.S. Pat. No. 3,668,217.
*[2] Commercially available fungicide known as "Captan".

EXAMPLE 6

Protective activity on rice blast (*Pyricularia oryzae*):

Rice plants (var: Kinki No. 33) were grown up to the beginning of the five-leaf stage in flower pots of 9 cm in diameter. Each test compound in the form of an emulsifiable concentrate was diluted with water to the required concentration and foliar-sprayed in a proportion of 15 ml/pot. After 1 day, a spore suspension of *Pyricu-*

*laria oryzae* was inoculated by spraying and kept at 25° C for 4 days in a constant temperature room with a high humidity. Thereafter, the disease severity was obtained from the percentage of infected area of the leaf, and the protective activity was checked. The results are shown in Table 5.

Table 5

| Test compound No. | Concentration (ppm) | Disease severity (%) | Control of disease (%) |
|---|---|---|---|
| 15 | 100 | 0 | 100 |
|  | 50 | 10.0 | 90 |
| 16 | 100 | 0 | 100 |
|  | 50 | 5.0 | 95 |
| 17 | 100 | 0 | 100 |
|  | 50 | 12.0 | 88 |
| 18 | 100 | 0 | 100 |
|  | 50 | 10.0 | 90 |
| O-Ethyl-S,S-diphenyl-dithiophosphate *[1] | 100 | 17.5 | 82 |
| No treatment | — | 100.0 | — |

Note:
*[1] Commercially available fungicide known as "EDDP".

| Symbol | Phytotoxicity |
|---|---|
| — | Not observed |
| ± | Not clear |
| + | Slight |
| ++ | Moderate |
| +++ | High |
| ++++ | Killed |

Table 6

| Test compound No. | Concentration (ppm) | Test plant | | | | | |
|---|---|---|---|---|---|---|---|
| | | Cucumber | Bean | Pimento | Egg-plant | Tomato | Chinese cabbage |
| 15 | 2000 | ± | — | — | — | ± | — |
|  | 500 | — | — | — | — | — | — |
| 16 | 2000 | — | — | — | — | — | — |
|  | 500 | — | — | — | — | — | — |
| 17 | 2000 | ± | — | — | ± | ± | — |
|  | 500 | — | — | — | — | — | — |
| 18 | 2000 | — | — | — | — | ± | — |
|  | 500 | — | — | — | — | — | — |
| (3,5-dichlorophenyl compound) | 2000 | +++ | ++ | ++ | ++++ | ++++ | +++ |
|  | 500 | + | + | + | ++ | ++ | + |
| No treatment | — | ± | — | — | ± | — | — |

Note:
*[1] Disclosed in U.S. Pat. No. 3,668,217.

EXAMPLE 7

Phytotoxicity test:

Phytotoxicities to cucumbers (var.: Kurume Ochiai H type), beans (var.: Nagauzura), pimentos (var.: Ace), eggplants (Var.: Senryo), tomatoes (var.: Fukuju No. 2) and chinese cabbages (var.: Nozaki No. 2) were tested according to the following method. The test plants used were those which had been grown up in a green-house for 1 to 2 months. Each test compound in the form of an emulsifiable concentrate was diluted with water to the required concentration and foliar-sprayed in a proportion of 20 ml/pot. After spraying, the pots were placed in a glass room for 1 week during which the temperature was kept at 23° C (night) to 32° C (daytime). Thereafter, the phytotoxicity was checked. The rate of phytotoxicity was classified as follows:

EXAMPLE 8

Test using white water:

Ten grams of each of the compounds (15) to (18) was dissolved in 100 ml of water, and 5 ml of each solution was diluted by adding to 1 liter of the white water obtained by the groundwood-pulp production process. Five milliliters of each dilute solution was further diluted by adding to 2 liters of the white water. To 100 ml of the test solution thus obtained were added 10 g of grape sugar, 1 g of peptone, 0.05 g of magnesium sulfate and 0.01 g of calcium chloride, and the mixture was sterilized by heating and inoculated with *Bacillus* spp. alone which was isolated from the slime resulting from a paper-making process. Propagation of the fungus was not observed at all, while a vigorous propagation was observed in the untreated plot within 24 hours.

What is claimed is:

1. A microbicidal composition which comprises a microbicidally effective amount of a compound of the formula:

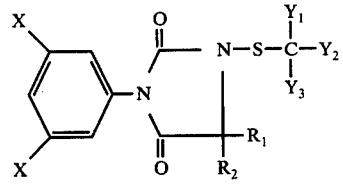

wherein X is a chlorine atom or a bromine atom, $Y_1$, $Y_2$ and $Y_3$ are each a chlorine atom or a fluorine atom and $R_1$ and $R_2$ are individually a hydrogen atom or a methyl group, and an inert carrier.

2. A method for controlling fungi which comprises applying a microbicidally effective amount of a compound of the formula:

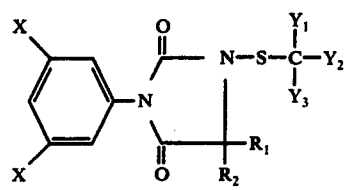
wherein X is a chlorine atom or a bromine atom, $Y_1$, $Y_2$ and $Y_3$ are each a chlorine atom or a fluorine atom and $R_1$ and $R_2$ are individually a hydrogen atom or a methyl group, to the fungi.
3. A compound of the formula:
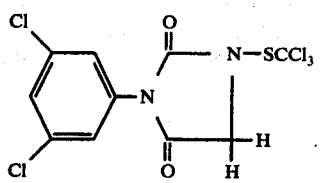
4. A compound of the formula:
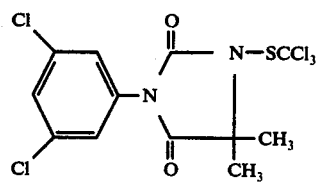
5. A compound of the formula:
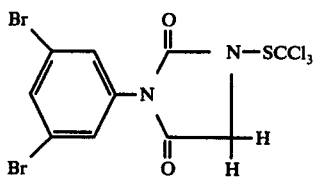
* * * * *